United States Patent [19]
Linhardt et al.

[11] Patent Number: 6,121,430
[45] Date of Patent: Sep. 19, 2000

[54] REGIOSPECIFIC SYNTHESIS OF GLUCOSE-BASED SURFACTANTS

[75] Inventors: Robert J. Linhardt; Helene G. Bazin, both of Iowa City, Iowa

[73] Assignee: University of Iowa Research Foundation, Iowa City, Iowa

[21] Appl. No.: 09/298,674

[22] Filed: Apr. 23, 1999

Related U.S. Application Data

[60] Provisional application No. 60/113,985, Dec. 28, 1998.

[51] Int. Cl.[7] .............................. C07G 3/00; C08B 37/02; C07H 1/00
[52] U.S. Cl. ......................... 536/4.1; 510/130; 510/151; 510/356; 510/357; 510/426; 510/476; 510/472; 510/473; 510/474; 536/1.11; 536/6; 536/17.2; 536/18.2; 536/18.6; 536/51; 536/54; 536/103; 536/112
[58] Field of Search .................................. 510/130, 151, 510/356, 357, 426, 470, 472, 473, 474; 536/1.11, 4.1, 6, 18.6, 51, 54, 103, 112, 17.2, 18.2

[56] References Cited

U.S. PATENT DOCUMENTS

| | | | |
|---|---|---|---|
| 4,115,094 | 9/1978 | Poller et al. | 71/88 |
| 4,950,746 | 8/1990 | Navia | 536/119 |
| 5,023,329 | 6/1991 | Neiditch et al. | 536/119 |
| 5,034,551 | 7/1991 | Vernon et al. | 556/89 |
| 5,089,608 | 2/1992 | Walkup et al. | 536/124 |
| 5,271,860 | 12/1993 | Schwadtke et al. | 252/96 |
| 5,470,969 | 11/1995 | Sankey et al. | 536/115 |
| 5,658,875 | 8/1997 | Giesen et al. | 510/470 |
| 5,663,137 | 9/1997 | Giesen et al. | 510/470 |
| 5,686,603 | 11/1997 | Au et al. | 536/123.13 |
| 5,756,446 | 5/1998 | Bator et al. | 510/535 |

FOREIGN PATENT DOCUMENTS 0352 048 A2  1/1990   European Pat. Off. .

OTHER PUBLICATIONS

S.David and S.Hanessian, Regiospecific Manipulation of Hydroxyl Groups Via Organotin Derivatives; Tetrahedron Report No. 180, vol. 41, No. 4, pp. 643–663, 1985, Great Britain No Month Given.

Abstract–Klotz W, Schmidt RR, KDO–Alph–Glycosides, Institute of Scientific Information, 1998, Germany No Month Given.

Helene G. Bazin, Tulay Polat, Robert J. Linhardt, Carbohydrate Research, Apr. 23, 1998, Elsevier Science Ltd., Oxford and New York.

*Primary Examiner*—Yogendra Gupta
*Assistant Examiner*—Brian P. Mruk
*Attorney, Agent, or Firm*—Zarley, McKee, Thomte, Voorhees & Sease

[57] ABSTRACT

New glucose-based surfactants and methods of their synthesis are described. The surfactants are synthesized through the preparation of an intermediate glucose 4,6-cyclic sulfate. The surfactants are economical to prepare and have excellent surface-active properties.

19 Claims, No Drawings

REGIOSPECIFIC SYNTHESIS OF GLUCOSE-BASED SURFACTANTS

CROSS-REFERENCE TO RELATED APPLICATION

This application is a continuation-in-part of provisional application Ser. No. 60/113,985 filed Dec. 28, 1998, the disclosure of which is hereby expressly incorporated by reference.

FIELD OF THE INVENTION

This invention relates to the synthesis of surfactants. More specifically, the invention describes the synthesis of new anionic and amphoteric glucose-based surfactants.

BACKGROUND OF THE INVENTION

Surface-active compounds, or surfactants, are widely used as wetting agents and detergents in industry, pharmaceutics, and in the home. Surfactants are compounds which, while soluble in a given liquid, tend to accumulate in the interfaces between this liquid and air, another immiscible liquid, or a solid. Because of their high concentration in these interfaces, surfactants lower the corresponding interfacial tensions or free energies.

Surfactants are amphiphiles because they contain a hydrocarbon (hydrophobic and lipophilic) portion and one or more ionic or otherwise strongly hydrophilic groups in the same molecule. This dual nature causes them to be preferentially adsorbed at air-water, oil-water, and solid-water interfaces, forming oriented monolayers in which the hydrophilic groups are in the aqueous phase and the hydrocarbon chains are pointed towards the air, in contact with the solid surface, or immersed in the oil phase.

As increasing amounts of a solid surfactant are dissolved in a beaker full of water and its concentration in solution increases, its monolayers adsorbed at the air-water and glass-water interfaces become more and more crowded until they are so tightly packed that further occupancy requires excessive compression of the surfactant molecules already in the two monolayers. Further increments in the amount of dissolved surfactant beyond that concentration cause amounts equivalent to the new molecules to aggregate into micelles. This process begins at a characteristic concentration called the critical micelle concentration (CMC). The CMC value is of practical importance since it is the minimal concentration of surfactant required to solubilize hydrophobic molecules in water.

From the time the CMC is reached, the concentration of monomeric or nonassociated surfactant molecules hardly increases, rising only slightly above the CMC, but the concentration of micellar or associated molecules increases in direct proportion to the increase in overall surfactant concentration. In dilute concentrations, the micelles are approximately of the same size. Increments in surfactant merely increase the number of micelles.

Surfactants are generally classified according to chemical structure. For convenience, they are categorized according to their polar portions since the nonpolar portion is usually made up of alkyl or aryl groups. The major polar groups found in most surfactants may be divided as follows: 1) anionic; 2) cationic; 3) amphoteric; and 4) nonionic.

The most commonly used anionic surfactants are those containing carboxylate, sulfonate, and sulfate ions. Those containing carboxylate ions are known as soaps and are generally prepared by the saponification of natural fatty acid glycerides in alkaline solution. The most common cations associated with soaps are sodium, potassium, ammonium, and triethanolamine, while the chain length of the fatty acids ranges from 12 to 18.

Amphoteric surfactants include those containing carboxylate or phosphate groups as the anion and amino or quaternary ammonium groups as the cation. The former group is represented by various polypeptides, proteins, and the alkyl betaines, while the latter group consists of natural phospholipids such as the lecithins and cephalins.

Most of the surfactants produced by the chemical industry are based on petrochemicals. A number of efforts to use carbohydrates as bulk raw materials for synthesis of nonionic surfactants have been reported. The amphiphilic behavior of petrochemicals is caused by the presence of the hydrophilic free hydroxyl groups and a hydrophobic alkyl chain.

Sugar surfactants are distinguished from other surfactants by their excellent detergent properties, non-toxicity, skin compatibility, environmental compatibility, and biodegradability. For these reasons, sugar surfactants are acquiring increasing significance.

Glucose is a monosaccharide having the following chemical structure:

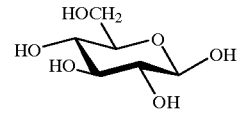

Most of the approaches in synthesizing sugar surfactants have been directed to the preparation of fatty acid esters of mono- and disaccharides. Vlahov I. R., et al., *Chem.* 1997, 16, 1 and references cited therein. Attempts to synthesize cyclic sulfates of unprotected sugars with sulfuryl chloride and pyridine have been reported. Bragg P. D. et al, *Can. J. Chem.* 1959, 37, 1412. However, this reaction is not clean, and several side products are isolated.

There is therefore a need in the art for a means of synthesizing regiospecific sugar-based surfactants in an efficient manner.

The present inventors have now discovered that the regioselective chemical introduction of fatty acid or fatty amine groups into glucose leads to surface-active neutral glucose esters.

It is therefore a primary objective of the present invention to provide a method and means of synthesizing glucose-based surfactants in high yields.

It is a further objective of the present invention to provide a method and means of synthesizing glucose-based surfactants that is regiospecific.

It is still a further objective of the present invention to provide a method and means of synthesizing glucose-based surfactants wherein the surfactants have excellent surface active properties.

It is yet a further objective of the present invention to provide a method and means of synthesizing glucose-based surfactants that is efficient and economical.

These and other objectives will become clear from the following detailed description of the invention.

SUMMARY OF THE INVENTION

The present invention relates to the regiospecific synthesis of a new class of anionic and amphoteric glucose-based surfactants. The O-acyl-O-sulfoglucose surfactants may be prepared through the preparation of an intermediate glucose cyclic sulfate. The surfactants are then synthesized through regiospecific nucleophilic displacement with fatty acids or amines.

The new glucose-based surfactants display exceptional surface-active properties with CMC values from two to three orders of magnitude lower than those of commercial anionic surfactants. These new surfactants are also biodegradable and may be economically prepared using inexpensive renewable starting materials.

BRIEF DESCRIPTION OF THE DRAWING

FIG. 1 is a reaction scheme for the synthesis of a methyl α-D-glucopyranoside cyclic sulfate through the reaction of methyl α-D-glucopyranoside with thionyl chloride and pyridine in DMF:ethyl acetate, which upon oxidation affords the cyclic sulfate.

DETAILED DESCRIPTION OF THE PREFERRED EMBODIMENT

This invention provides an improved and more efficient means for synthesizing glucose-based emulsifiers and surfactants wherein the process of the invention is highly regioselective. The terms "regioselective" or "regiospecific" herein refer to a reaction that highly favors a single major product.

The invention describes the synthesis of new glucose-based surfactants. The synthesis method involves nucleophilic displacement of intermediate glucose cyclic sulfates with various fatty acids or amines.

Glucose cyclic sulfates may be prepared in a variety of manners. The sulfates may either be prepared directly or through the preparation of an intermediate cyclic sulfite followed by oxidation.

Attempts to synthesize cyclic sulfates of unprotected sugars with sulfuryl chloride and pyridine have been reported. Bragg P. D. et al, *Can. J. Chem.* 1959, 37, 1412. However, this reaction is not clean, and several side products are isolated. For example, reaction of sucrose with sulfuryl chloride at −78° C. afforded the 6,6'-dichloro-6,6'-deoxysucrose and 6'-chloro-6'-deoxysucrose in 43 and 29% yields, respectively. At room temperature, a complex mixture was formed from which 3',4'-anhydro-1',6'-dichloro-1',6'-dideoxy-β-D-ribo-hexulofuranoside. 2,3-cyclic sulfate was isolated in 17% yield, showing that chlorination occurred as well as inversion of configuration during cyclic sulfate formation. Ballard J. M, et al., *J. Chem. Soc., Perkin Trans.* 1, (1973) 1524–1528.

Another method of cyclic sulfate synthesis is through the conversion of a vicinal cis diol system to a cyclic sulfate in protected carbohydrates with sulfuryl chloride. See e.g. van der Klein P. A. M., et al., *Tetrahedron Lett.,* 30 (1989) 5477–5480.

The reaction of diols with thionyl chloride ($SOCl_2$) in the presence of an amino base give cyclic sulfites directly and in good yield, unlike the analogous reaction with sulfuryl chloride($SO_2Cl_2$), which usually results in only very low yields of the corresponding sulfates. Gao Y., et al., *J. Am. Chem. Soc.,* 110 (1988) 7538–7539. This cyclic sulfate synthesis method is therefore preferred.

Preparation of glucose cyclic sulfates does not require protection of the hydroxyl groups. Instead, glucose cyclic sulfites or sulfates may be directly synthesized using any of the methods described above. Formation of the cyclic sulfite with thionyl chloride followed by oxidation to form the cyclic sulfate is the preferred method.

Glucose cyclic sulfates may be prepared through the direct reaction of glucose with, for example, thionyl chloride. Glucose derivatives are also appropriate for use in this reaction. The pyranose form of glucose is preferred. A preferred method involves the reaction of thionyl chloride with methyl α-D-glucopyranoside.

Cyclic sulfates are readily prepared through the oxidation of cyclic sulfites. Permanganate oxidation of the sulfite was originally the favored route to cyclic sulfates. In 1981, it was reported that the oxidation step was much cleaner when affected by a stoichiometric amount of ruthenium (IV) tetraoxide ($RuO_4$). Denmark D. E., *J. Org. Chem.,* 46 (1981) 3144–3147. Gao and Sharpless reported the use of a catalytic amount of ruthenium (III) trichloride ($RuCl_3$) with $NaIO_4$ as a preparative method for the synthesis of cyclic sulfates from cyclic sulfites. Gao Y., et al. (1988). These sulfate preparation methods are most preferred for use in the present invention.

Another approach for the synthesis of cyclic sulfites and sulfates from protected carbohydrates relies on the use of N,N'-thionyldiimidazole or N,N'-sulfuryldiimidazole, respectively. Lowe G., et al., *J. Chem. Soc., Chem. Commun.,* (1983) 1392–1394; Williams E. H. et al., *Can. J. Chem.,* 49 (1971) 796–799. This chemistry, however, requires the use of a strong base, such as NaH, and is therefore less preferred.

Phenyl chlorosulfate has also been reported to give the corresponding cyclic sulfate of protected sugars in 60–70% yields. El Meslouti A., et al., *Tetrahedron Lett.,* 35 (1994) 3913–3916. Only 1,2-cyclic sulfites of the unprotected carbohydrates, glucose, galactose and mannose, have been synthesized using N,N'-thionyldiimidazole. These cyclic sulfites were reportedly unstable and were used in situ in the reaction with azide.

Klotz and Schmidt recently reported the use of cyclic sulfate to prepare sugar-based surfactants. Klotz W., et al., *Synthesis,* (1996) 687–689. However, the cyclic sulfates synthesized from 1,2-fatty diols, were used for alkylation of glucose to obtain anomeric alkyl glycosides.

Once the intermediate glucose 4,6-cyclic sulfate is formed, the next step is displacement of the cyclic sulfate.

Nucleophilic displacement of glucose cyclic sulfates is accomplished by reacting the cyclic sulfate with an excess of a fatty acid or a fatty amine. Nucleophilic displacement of this glucose cyclic sulfate by different fatty acids and amines leads to the corresponding methyl 6-O-acyl- or 6-amino-6-deoxy-4-sulfoglucopyranosides in excellent yields.

Appropriate fatty acids and amines for nucleophilic displacement include the $C_4$–$C_{24}$ fatty acids and amines. $C_6$–$C_{16}$ fatty acids and amines are preferred.

Synthesis of compounds in accordance with the present invention results in glucose-based surfactants in good to excellent yields. In addition, the surfactants have been found to have exceptional surface-active properties. In fact, these new anionic and amphoteric surfactants have CMC values from two to three orders of magnitude lower than the CMC values of commercial surfactants.

The new surfactants are economical to manufacture since they are prepared using inexpensive renewable starting materials. Moreover, since the surfactants are sugar-based, they are biodegradable and non-toxic to the user.

The surfactants of this invention may be used for the same purposes and in the same manner as other commercial surfactants. Since the glucose-based surfactants are non-toxic, they are especially appropriate for use in the cosmetics industry and in pharmaceutical formulations, including oral, dermatological, and intravenous formulations, as wetting, solubilizing, and emulsifying agents. Typical concentrations of surfactants in pharmaceuticals and cosmetics ranges from about 0.1–40.0% by weight, with from about 0.1–5.0% being preferred. Of course, this amount will vary according to the composition of the pharmaceutical and/or cosmetic and its intended use.

The following examples are presented for informational purposes only. They are not intended to limit the scope of the invention in any manner.

EXAMPLE 1

Synthesis of Methyl α-D-glucopyranoside Cyclic Sulfate

Synthesis of a methyl α-D-glucopyranoside cyclic sulfate relied on the two-step procedure set forth in FIG. 1. Reaction of methyl α-D-glucopyranoside 1 with thionyl chloride ($SOCl_2$) and pyridine in DMF:ethyl acetate (v/v 1:1) at room temperature for 1.5 h afforded the corresponding 4,6-cyclic sulfite 2 in 70% yield, after purification on silica gel (Table 1). The position of the cyclic sulfite as well as the configuration of the sulfoxide group was determined by 'H NMR[5]. The significant deshielding[9] of H-4 and H-6a indicates (i) a 4,6-cyclic sulfite and (ii) the axial configuration of the sulfoxide group. The equatorial isomer was not formed under these reaction conditions. Oxidation of 3 in acetonitrile:water (v/v 1:1.5) using sodium periodate ($NaIO_4$) with a catalytic amount of ruthenium (III) chloride ($RuCl_3$) led to the 4,6-cyclic sulfate 3 in 82% yield.

EXAMPLE 2

Synthesis of Methyl 6-O-lauroyl-4-O-sulfo-α-D-glucopyranoside

Reaction of the cyclic sulfate 3 in DMF with a slight excess of lauric acid and potassium bicarbonate for 3 h at 70° C. afforded the methyl 6-O-lauroyl-4-O-sulfo-α-D-glucopyranoside 4 in 85% yield. The 4-position of the O-sulfonation was confirmed by acid catalyzed hydrolysis of the sulfo group in 4. The 'H NMR spectrum of the resulting product showed a large upfield shift for H-4 ($\Delta\delta$=−0.95 ppm) while H-5, H-6a and H-6b were moderately shifted ($\Delta\delta$=+0.1, −0.30 and +0.10 ppm, respectively). The same reaction performed with myristic and palmitic acids under identical conditions led to the 6-O-myristoyl- and 6-O-palmitoyl-4-O-sulfo derivatives 5 and 6 in 91% and 87% yield, respectively (Table 1, FIG. 1).

EXAMPLE 3

Synthesis of 6-deoxy-6-hexylamino-, 6-deoxy-6-decylamino- and 6-deoxy-6-tetradecylamino-4-O-sulfo Derivatives Reaction of the cyclic sulfate 3 with a slight excess of hexylamine, decylamine or tetradecylamine in DMF at 80° C. for 17 h, led to the corresponding amphoteric 6-deoxy-6-hexylamino-, 6-deoxy-6-decylamino- and 6-deoxy-6-tetradecylamino-4-O-sulfo derivatives 7, 8 and 9 in 53%, 51% and 54% yield, respectively (Table 1, FIG. 1).

A dye solubilization method was used to determine the CMC of the sulfated surfactants. The newly synthesized water soluble acylsulfo and aminosulfo products 4, 5, 6, and 7 displayed excellent surface-active properties (Table 2).

In aqueous solution, at a specific concentration known as the critical micellar concentration (CMC), surfactant molecules aggregate in micelles. This CMC value is of practical importance since it is the minimal concentration of surfactant required to solubilize hydrophobic molecules in water. A calorimetric method for CMC determination using a dye solubilization method was used to determine the CMC of the sulfated surfactants. The newly synthesized water soluble acylsulfo and aminosulfo products 4, 5, 6 and 7, displayed excellent surface-active properties (Table 2). The CMC values determined for compounds 4–9 and the CMC values reported from the literature were measured at 25° C. for aqueous solutions of the surfactants. The CMC values measured for the acylsulfo derivatives 4, 5 and 6 of $4.3 \times 10^{-4}$, $6.7 \times 10^{-5}$ and $3.4 \times 10^{-5}$ M respectively, were 1–2 orders of magnitude lower than those of commercially prepared ionic surfactants, the palmitoyl derivative showing the highest surface activity (Table 2). As expected, the CMC values decrease with acyl chain length. Amphoteric derivative 7 displayed a CMC value comparable to commercial surfactants while compounds 8 and 9 were insufficiently water soluble to determine their CMC values.

TABLE 2

CMC Values of Compounds 4–9 and Commercially Available Surfactants

| Compounds | CMC mmol/L | CMC mg/L |
|---|---|---|
| 4 | 0.43 | 210 |
| 5 | 0.067 | 35 |
| 6 | 0.034 | 20 |
| 7 | 3.0 | 1200 |
| 8 | ns | ns |
| 9 | ns | ns |
| $C_{10}H_{21}OC_2H_4SO_3Na$ | 15.9 | 4600 |
| $C_{12}H_{25}SO_3Na$ | 12.4 | 3400 |
| $C_{12}H_{25}OSO_3Na$ | 7.94 | 2300 |
| $C_{12}H_{25}OC_2H_4OSO_3Na$ | 3.91 | 1300 |
| Octyl β-D-glucopyranoside | 25.1 | 7400 |

New O-acyl-O-sulfo and amino-O-sulfoglucopyranoside-based surfactants have been synthesized by nucleophilic displacement of the methyl α-D-glucopyranoside 4,6-cyclic sulfate with fatty acids and amines. These new anionic surfactants display very good surface active properties with CMC values from one to two orders of magnitude lower than those of commercial anionic surfactants. They are readily prepared using inexpensive renewable starting materials in high yield and in only 2 reaction steps without the requirement of hydroxyl protection. These derivatives display very good surface active properties, should be biodegradable and thus, may have commercial applications as both surfactants and detergents.

TABLE 1

Yields and Physical Characteristics of Compounds 2–9

| Compounds | Yields (%) | $[\alpha_D]^{24}$ | mp (° C.) | HRFABMS | IR (cm$^{-1}$) | $^1$H NMR (500 MHz) (Solvent) |
|---|---|---|---|---|---|---|
| 2 | 70 | +135 (c 2, MeOH) | 163–165 | Calcd. 263.0201[a] Found 263.0202 | 1031 (O$_2$SO), 2832 (OCH$_3$), 3200–3600 (OH) | (CDCl$_3$) δ 3.48(s, 3H, OMe), 3.57(dd, 1H, J$_{1,2}$ 3.8Hz, J$_{2,3}$ 9.3Hz, H-2), 3.83(t, 1H, J$_{3,4}$ 9.5Hz, H-3), 3.98(m, 1H, H-5), 4.02(dd, 1H, J$_{5,6b}$ 4.9Hz, J$_{6a,b}$ 10.1Hz, H-6b), 4.51(t, 1H, J4,5 9.6Hz, H-4), 4.63(t, 1H, J$_{5,6a}$ <1.0Hz, H-6a, 4.76(d, 1H, H-1). |
| 3 | 82 | +131 (c 1, MeOH) | 160–162 | Calcd. 279.0150[a] Found 279.0153 | 1035 and 1220 (O$_2$SO$_2$), 2837 (OCH$_3$), 3200–3500 (OH) | (CDCl$_3$): 3.46(s, 3H, OMe), 3.53(dd, 1H, J$_{1,2}$ 3.7Hz, J$_{2,3}$ 9.3Hz, H-2), 3.88(t, 1H, J$_{3,4}$ 9.3Hz, H-3), 4.14(m, 1H, H-5), 4.41(t, 1H, J$_{4,5}$ 9.8Hz, H-4), 4.56–4.62(m, 2H, J$_{6a,b}$ 10.4Hz, H-6a and H-6b), 4.77(d, 1H, H-1). |
| 4 | 85 | +62 (c 1, MeOH) | 215–217 (d) | Calcd. 455.1951[b] Found 455.1953 | 1034 (OSO$_3^-$), 1420–1460 and 2910–2960 (CH$_2$ and CH$_3$), 1725 (OC(O)R), 3200–3500 (OH) | (CD$_3$OD): δ 0.90(y, 3H, CH$_3$), 1.23–1.38(m, 16H, 8CH$_2$), 1.63(quint., 2H, C(O)CH$_2$CH$_2$), 2.35(t, 2H, C(O)CH$_2$), 3.42(s, 3H, OMe), 3.54 (dd, 1H, J$_{1,2}$ 3.7Hz, J$_{2,3}$ 9.8Hz, H-2), 3.84(m, 1H, H-5), 4.00(t, 1H, J$_{3,4}$ 9.5Hz, H-3) 4.17(dd, 1H, J$_{4,5}$ 8.9Hz, H-4), 4.26(dd, 1H, J$_{5,6b}$ 6.2Hz, J$_{6a,b}$ 12.1Hz, H-6b), 4.41(t, 1H, J$_{5,6a}$ 2.1Hz, H-6a), 4.68(d, 1H, H-1). |
| 5 | 91 | +62 (c 1, MeOH) | 207–209 (d) | Calcd. 483.2264[b] Found 483.2267 | Signals identical to those of 4 | (CD$_3$OD) δ 0.89(t, 3H, CH$_3$), 1.25–1.35(m, 20H, 10CH$_2$), 1.62(quint., 2H, C(O)CH$_2$CH$_2$), 2.35(t, 2H, C(O)CH$_2$); other signals identical with those of 4. |
| 6 | 87 | +77 (c 1, MeOH) | 204–206 (d) | Calcd. 511.2577[b] Found 511.2574 | Signals identical to those of 4 | (CD$_3$OD) δ 0.89(t, 3H, CH$_3$), 1.22–1.38(m, 24H, 12CH$_2$), 1.61(quint., 2H, C(O)CH$_2$CH$_2$), 2.35(t, 2H, C(O)CH$_2$); other signals identical with those of 4. |
| 7 | 53 | +116 (c 0.5, MeOH) | amorphous glass | Calcd. 356.1379[b] Found 356.1382 | Signals identical to those of 9 | (CD$_3$OD) δ 0.89(t, 3H, CH$_3$), 1.25–1.43(m, 6H, 3CH$_2$), 1.75(quint., 2H, NCH$_2$CH$_2$), 3.01(t, 2H, NCH$_2$); other signals identical with those of 9. |
| 8 | 51 | +74 (c 1, MeOH) | 194–196 (d) | Calcd. 412.2005[b] Found 412.2002 | Signals identical to those of 9 | (CD$_3$OD) δ 0.90(t, 3H, CH$_3$), 1.25–1.37(m, 14H, 7CH$_2$), 1.72(quint., 2H, NCH$_2$CH$_2$), 3.02(t, 2H, NCH$_2$); other signals identical with those of 9. |
| 9 | 54 | +74 (c 1, v/v 1:1 MeOH:CHCl$_3$) | 209–212 (d) | Calcd. 468.2631[b] Found 468.2627 | 763 and 1660 (NH$_2^+$), 1035 (OSO$_3^-$), 1420–1460 and 2910–2960 (CH$_2$ and CH$_3$), 3200–3500 (OH) | (CD$_3$OD) δ 0.89(t, 3H, CH$_3$), 1.25–1.43(m, 22H, 11CH$_2$), 1.75(quint., 2H, NCH$_2$CH$_2$), 3.01(t, 2H, NCH$_2$), 3.30(dd, 1H, J$_{5,6b}$ 6.3Hz, J$_{6a,b}$ 13.3Hz, H-6b), 3.42(dd, 1H, J$_{5,6a}$ 3.1Hz, H-6a), 3.38(s, 3H, OMe), 3.55(dd, 1H, J$_{1,2}$ 3.7J$_{2,3}$ 9.6Hz, H-2), 3.86(t, 1H, J$_{3,4}$ 9.3Hz, H-3), 3.94(m, 1H, J$_{5,6b}$ 6.2Hz, H-5), 4.11(dd, 1H, J$_{4,5}$ 8.2Hz, H-4), 4.75(d, 1H, H-1). |

[a]Mass calculated for [M + Na$^+$]$^+$;
[b]Mass calculated for [M − H]$^-$

General Experimental Procedures for Examples 1–4

Nuclear magnetic resonance ($^1$H NMR) spectra were recorded at 25° C. in deuteried solvent on a Varian Unity 500 MHz spectrometer. Chemical shifts were recorded in ppm (δ) and coupling constants in Hz, relative to tetramethylsilane as internal standard. The $^1$H NMR spectra were fully assigned by the use of single-frequency decoupling. Optical rotations were measured with a Jasco P-1020 polarimeter. Thinlayer chromatography (TLC) was performed using E. Merck plates of Silica Gel 60 with fluorescent indicator. Visualization was effected by spraying plates with Von's reagent (1.0 g of ceric ammonium sulfate and 24.1 g of ammonium molybdate in 31 mL of sulfuric acid and 470 mL of water), followed by heating at 140° C. Flash chromatography was conducted with silica gel (230–430 mesh, E. Merck). Anhydrous DMF, ethyl acetate (EtOAc), pyridine and methyl α-d-glucopyranoside were from Aldrich. The colorimetric CMC determination used uniformly precoated plastic balls that were purchased from Pro Chem, Inc. (Rockford, Ill.). The absorption of the dye was measured at 612 nm on Shimadzu UV-60. All the sulfoglucopyranoside derivatives were hygroscopic, preventing their elemental analysis. The purity and identity of these surfactants were assessed based on the absence of extraneous signals in their $^1$H NMR spectra and on the expected molecular ion by high-resolution mass spectrometry.

Methyl α-D-glucopyranoside 4,6-cyclic sulfite 2

To a solution of methyl α-D-glucopyranoside (1.0 g, 5.15 mmol) in anhydrous DMF:EtOAc (v/v 1:2, 12 mL) and under nitrogen, SOCl$_2$ (0.39 mL, 5.41 mmol) and anhydrous pyridine (0.87 mL, 10.81 mmol) were added.

After 45 min at room temperature, SOCl$_2$ (0.18 mL, 2.52 mmol) and anhydrous pyridine (0.43 mL, 1.25 mmol) were added. After an additional 45 minutes, the reaction mixture was neutralized by addition of triethylamine and the solvent evaporated in vacuo. Purification by chromatography on silica gel (MeOH—CHCl v/v, 1:15) afforded 2 (865 mg, 70%) as a white solid.

Methyl α-D-glucopyranoside 4,6-cyclic sulfate 3

To a solution of 2 (62 mg, 0.26 mmol) in a mixture of H$_2$O—CH$_3$CN (v/v 1:1.5, 2.5 mL), RuCl$_3$ (catalytic amount) and NaIO$_4$ (110 mg, 0.51 mmol) were added. After 1 h at room temperature the reaction mixture was concentrated in vacuo. Purification by chromatography on silica gel (MeOH—CHCl$_3$v/v, 1:9) afforded 3 (54mg, 82%) as a white solid.

Synthesis of Methyl 6-O-acyl-4-O-sulfo α-D-glucopyranoside Derivatives 3–5; General Procedure To a solution of 3 (50 mg, 0.19 mmol) in anhydrous DMF (4 mL) maintained under nitrogen, $K_2CO_3$ (1.2 equiv) and the fatty acid (1.2 equiv were added). The reaction mixture was heated at 70° C. for 3 h. After cooling at room temperature, the reaction mixture was filtered through Celite and evaporated in vacuo. Purification by chromatography on silica gel ($CHCl_3$—$CH_3OH$ v/v, 4:1) afforded the corresponding 6-O-acyl-4-O-sulfo α-D-glucopyranoside derivatives.

Synthesis of Methyl 6-O-alkylamino-6-O-deoxy-4-O-sulfo α-D-glucopyranoside Derivatives 6–9; General Procedure To a solution of 3 (50 mg, 0.19 mmol) in anhydrous DMF (4 mL) maintained under nitrogen, the fatty amine (1.2 equiv) was added. The reaction mixture was heated at 80° C. for 17 h and evaporated in vacuo. Purification by chromatography on silica gel ($CHCl_3$—$CH_3OH$ v/v, 4:1) afforded the corresponding 6-O-alkylamino-6-O-deoxy-4-O-sulfo α-D-glucopyranoside derivatives.

It is therefore submitted that the present invention accomplishes at least all of its stated objectives.

What is claimed is:

1. A method of synthesizing glucose-based surfactants having the following structure:

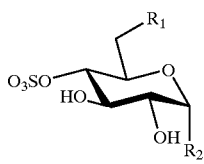

wherein:
   $R_1$ is selected from the group consisting of acyl and alkylamino; and
   $R_2$ is selected from the group consisting of alkoxy and acyl,
comprising:
   preparing a glucose 4,6-cyclic sulfate; and
   displacing the cyclic sulfate with a nucleophile.

2. A method according to claim 1 further including the steps of:
   preparing a glucose cyclic sulfite; and
   oxidizing the cyclic sulfite to form the glucose 4,6-cyclic sulfate.

3. A method according to claim 2 further including the steps of:
   obtaining a quantity of glucose or derivatives thereof;
   reacting the glucose with thionyl chloride to form the glucose cyclic sulfite.

4. A method according to claim 3 wherein the glucose derivative is methyl α-D-glucopyranoside.

5. A method according to claim 2 wherein the cyclic sulfite is oxidized in the presence of a catalytic amount of ruthenium (III) chloride.

6. A method according to claim 1 wherein the cyclic sulfate is displaced by reacting the cyclic sulfate with a nucleophile selected from the group consisting of a fatty acid and a fatty amine.

7. A method according to claim 6 wherein the fatty acid or fatty amine is a $C_4$–$C_{24}$ fatty acid or amine.

8. A method according to claim 7 wherein the fatty acid or fatty amine is a $C_6$–$C_{16}$ fatty acid or amine.

9. A glucose-based surfactant having the following structure:

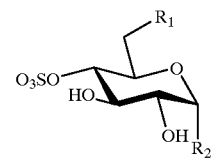

wherein:
   $R_1$ is selected from the group consisting of acyl and alkylamino; and
   $R_2$ is selected from the group consisting of alkoxy and acyl.

10. A surfactant according to claim 9 wherein the acyl group is a $C_4$–$C_{24}$ acyl group.

11. A surfactant according to claim 10 wherein the acyl group is a $C_6$–$C_{16}$ acyl group.

12. A surfactant according to claim 9 wherein the alkylamino group is a $C_4$–$C_{24}$ alkylamino group.

13. A surfactant according to claim 12 wherein the alkylamino group is a $C_6$–$C_{16}$ alkylamino group.

14. A surfactant according to claim 9 wherein the alkoxy group is methoxy.

15. A surfactant according to claim 9 wherein the acyl group is selected from the group consisting of lauroyl, myristoyl, and palmitoyl.

16. A surfactant according to claim 9 wherein the alkylamino group is selected from the group consisting of tetradecylamino, hexylamino, and decylamino.

17. A surfactant according to claim 9 which is a 6-O-acyl-4-O-sulfo α-D-glucopyranoside derivative or a 6-O-alkylamino-6-O-deoxy-4-O-sulfo α-D-glucopyranoside derivative.

18. A pharmaceutical composition comprising:
   a pharmaceutically active ingredient; and
   a glucose-based surfactant having a structure according to the surfactant of claim 9.

19. A cosmetic composition comprising:
   a cosmetic; and
   a glucose-based surfactant having a structure according to the surfactant of claim 9.

* * * * *